(12) United States Patent
McLaughlin (10) Patent No.: US 11,903,764 B2
(45) Date of Patent: *Feb. 20, 2024

(54) WIRELESS TRANSDUCER CHARGING FOR HANDHELD ULTRASOUND SYSTEMS

(71) Applicant: Shenzhen Mindray Bio-Medical Electronics Co., Ltd., Shenzhen (CN)

(72) Inventor: Glen W. McLaughlin, San Carlos, CA (US)

(73) Assignee: Shenzhen Mindray Bio-Medical Electronics Co., Ltd., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/862,047

(22) Filed: Jul. 11, 2022

(65) Prior Publication Data
US 2022/0370043 A1    Nov. 24, 2022

Related U.S. Application Data

(63) Continuation of application No. 16/358,344, filed on Mar. 19, 2019, now Pat. No. 11,464,486.

(51) Int. Cl.
| | |
|---|---|
| *A61B 8/00* | (2006.01) |
| *A61B 8/14* | (2006.01) |
| *A61B 8/08* | (2006.01) |
| *H02J 50/80* | (2016.01) |
| *H02J 50/10* | (2016.01) |

(52) U.S. Cl.
CPC .............. *A61B 8/4472* (2013.01); *A61B 8/14* (2013.01); *A61B 8/4427* (2013.01); *A61B 8/462* (2013.01); *A61B 8/5207* (2013.01); *A61B 8/56* (2013.01); *A61B 8/565* (2013.01); *H02J 50/80* (2016.02); *H02J 50/10* (2016.02)

(58) Field of Classification Search
CPC ....... A61B 8/4472; A61B 8/14; A61B 8/4427; A61B 8/462; A61B 8/5207; A61B 8/56; A61B 8/565; A61B 8/461; A61B 8/4444; A61B 8/4455; H02J 50/80; H02J 50/10; H02J 50/15; H02J 2310/23; H02J 7/00; H02J 50/00

See application file for complete search history.

(56) References Cited

U.S. PATENT DOCUMENTS

| | | |
|---|---|---|
| 7,443,057 B2 | 10/2008 | Nunally |
| 8,024,012 B2 | 9/2011 | Clevenger et al. |
| 8,099,140 B2 | 1/2012 | Arai |

(Continued)

FOREIGN PATENT DOCUMENTS

| | | | |
|---|---|---|---|
| CN | 02626321 | * | 8/2012 |
| KR | 101766648 | * | 8/2017 |

*Primary Examiner* — Yi-Shan Yang
*Assistant Examiner* — Alexei Bykhovski
(74) *Attorney, Agent, or Firm* — Kory D. Christensen (57) ABSTRACT

A wireless handheld ultrasound system an ultrasound front end to transmit ultrasonic waves into a subject and convert received ultrasonic echoes into digital data; an image processor coupled to the ultrasound front end to convert the digital data into an image; and a power section coupled to the ultrasound front end and the image processor. The power section may include a battery; a charging circuit to charge the battery; and a wireless power transducer coupled to the charging circuit to convert wireless power received from an external source into electrical energy for the charging circuit.

16 Claims, 4 Drawing Sheets

(56) References Cited

U.S. PATENT DOCUMENTS

| | | | |
|---|---|---|---|
| 8,760,113 B2* | 6/2014 | Keating | H02J 50/12 |
| | | | 320/108 |
| 9,362,783 B2 | 6/2016 | Lee et al. | |
| 9,444,283 B2 | 9/2016 | Son et al. | |
| 9,941,752 B2 | 4/2018 | Bell et al. | |
| 10,105,124 B2* | 10/2018 | Tashiro | A61B 8/4477 |
| 10,128,699 B2* | 11/2018 | Leabman | H02J 50/20 |
| 2007/0239001 A1 | 10/2007 | Mehi | |
| 2014/0276069 A1* | 9/2014 | Amble | A61B 8/4488 |
| | | | 600/447 |
| 2014/0323861 A1* | 10/2014 | Jin | H02J 50/12 |
| | | | 367/137 |
| 2014/0364741 A1 | 12/2014 | Cho | |
| 2016/0006291 A1* | 1/2016 | Li | H02J 50/90 |
| | | | 320/108 |
| 2017/0077765 A1 | 3/2017 | Bell | |
| 2017/0179774 A1* | 6/2017 | Jin | A61B 8/4472 |
| 2017/0358950 A1 | 12/2017 | Zeine | |
| 2018/0256905 A1* | 9/2018 | Francia | A61N 1/3956 |
| 2019/0027975 A1* | 1/2019 | Plasmans | H02J 50/80 |
| 2020/0127501 A1* | 4/2020 | Song | H02M 7/48 |

* cited by examiner

WIRELESS TRANSDUCER CHARGING FOR HANDHELD ULTRASOUND SYSTEMS

CROSS-REFERENCE TO RELATED APPLICATIONS

This application is a continuation of U.S. patent application Ser. No. 16/358,344, filed Mar. 19, 2019, for WIRELESS TRANSDUCER CHARGING FOR HANDHELD ULTRASOUND SYSTEMS, which is incorporated herein by reference.

TECHNICAL FIELD

The present disclosure relates to ultrasound imaging and, in particular, to wireless transducer charging for handheld ultrasound systems.

BACKGROUND

Figure 2:
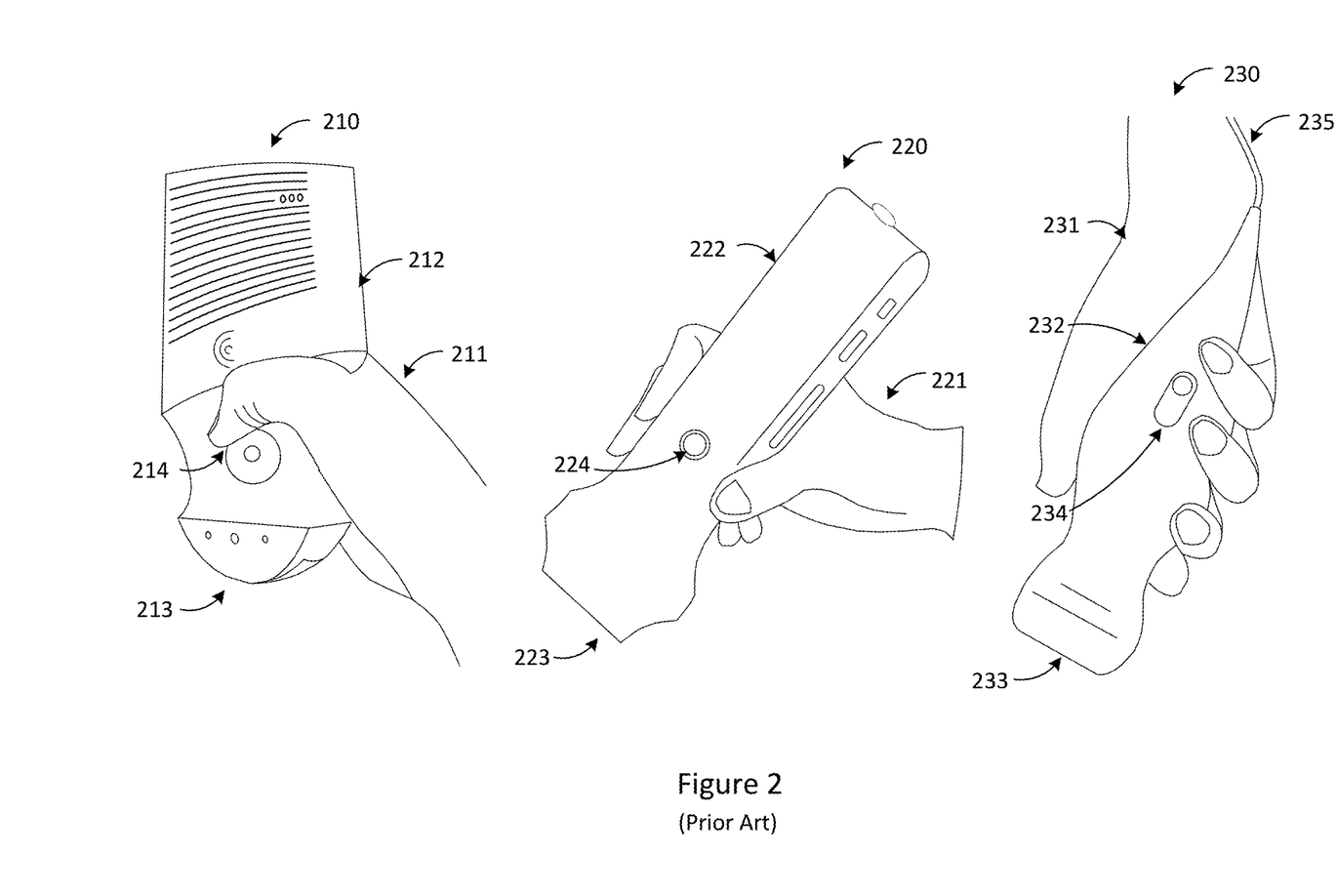
FIG. 2 is an external view of various wireless handheld ultrasound systems.

Handheld ultrasound systems that incorporate the entire imaging platform, as well as power source, within an ultrasonic probe have typically been larger and heavier than traditional wired ultrasonic probes, exhibiting poorer performance, shorter battery operation times, and greater heat generation. FIG. 2 illustrates three such handheld ultrasound systems 210, 220, 230, two of which are wireless and one which includes a wired interface.

The wireless handheld ultrasound systems 210, 220 tend to be large and uncomfortable to use for an extended period of time. For example, system 210 is shown held by a hand 211 for a size reference. It is clear that the hand 211 would have a difficult time being able to completely grasp the entire system 210. Not only is operating such a system 210 uncomfortable, but it can also be difficult to position at some angles in order to capture certain types of images. Standard parts of the system 210 include a processing section and battery (not shown), a communication section 212, a transducer 213, and a control section 214.

A second wireless handheld ultrasound system 220 is relatively slimmer than the first 210, but is longer as compared to the reference hand 221 holding the system 220. While easier to grasp, the length of the system 220 may also interfere with the capture of certain types of images. The second system 220 has similar components to the first 210, including a processing section and battery (not shown), communication section 222, transducer 223, and control section 224.

By contrast, the wired handheld ultrasound system 230 is relatively smaller compared to the representative hand 231. Note that this system 230 still contains the imaging platform and produces images internally. However, in addition to the standard communication section 232, transducer 233, and control section 234, the system 230 also includes a wired interface 235 for transmitting processed images for display or storage.

Figure 3:
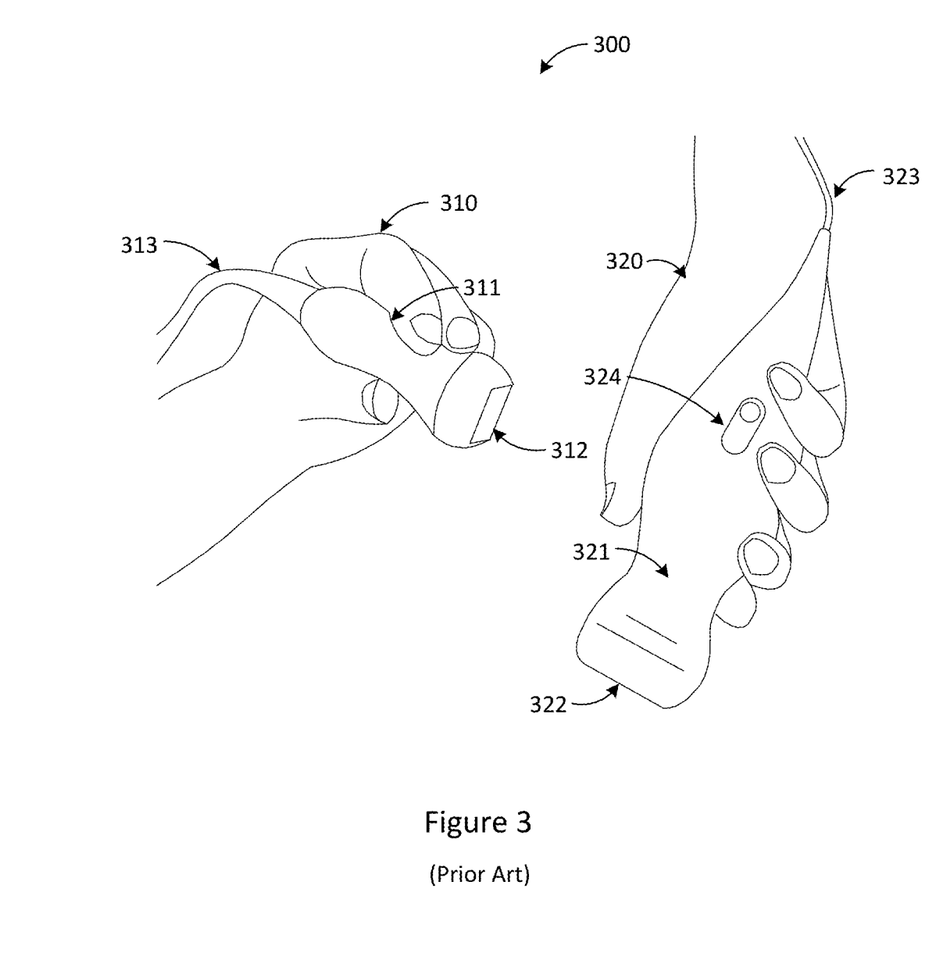
FIG. 3 compares a wireless handheld ultrasound system with a traditional wired phased array transducer.

FIG. 3 provides a comparison between a traditional phased array ultrasonic probe 311 and a handheld ultrasound system 321 with a wired interface 323, which is similar to the system 230 shown in FIG. 2. Compared to the reference hand 310, the traditionally phased array ultrasound probe 311 is relatively small. It can be seen that the hand 310 is in a comfortable and relaxed position while grasping the body of the probe 311. The electromechanical elements the probe 311 are shown, including the transducer 312 and a substantial cable 313 to bring raw signals back to the ultrasound system (not shown) for image processing.

When comparing the traditional ultrasonic probe 311 with that of a handheld ultrasonic system 321 that does processing internally, it can be seen that the size increases as shown by the hand 320 gripping the body of the probe 321. The wired handheld ultrasound system 321 also has a transducer 322, controls 324, and a much smaller cable 323, because much of the signal conditioning and processing is done in the body of the handheld system 321 so only digital data is required to be transmitted to the display unit.

Recently, attempts have been made using high level-integration circuits to incorporate the ultrasound transducer element into a single integrated circuit. This has resulted in dramatic improvements in size, performance, and heat generation, but has not significantly addressed the aspects of weight and operation time.

In order to improve the operation time, designers have continued to place larger batteries in these devices negating some of the other gains from the high-level single chip integration. Given the episodic use pattern of these products by clinicians, the absolute energy storage of the battery typically does not need to be able to cover an 8 or 10 hour shift, but needs to be sufficient for a little less than an hour of continuous operation for very demanding portions of the day. Having the system continually being charged independent of the placement of the handheld ultrasound unit (i.e., in the user's hand, pocket, on desk) would be a significant advancement over the current workflow of these systems.

SUMMARY

A wireless handheld ultrasound system according to the present disclosure includes an ultrasound front end to transmit ultrasonic waves into a subject and convert received ultrasonic echoes into digital data; an image processor coupled to the ultrasound front end to convert the digital data into an image; and a power section coupled to the ultrasound front end and the image processor. The power section may include a battery; a charging circuit to charge the battery; and a wireless power transducer coupled to the charging circuit to convert wireless power received from an external source into electrical energy for the charging circuit.

The ultrasound front end may include a transducer port; a transmitter to generate an electrical transmit waveform; a transmit/receive switch to convey the electrical transmit waveform to the transducer port during a transmit mode; and an ultrasound transducer coupled to receive the electrical transmit waveform from the transducer port and generate therefrom ultrasonic waves for transmission into the subject. The ultrasound transducer also converts ultrasonic echoes received from the subject into an electrical signal.

In one embodiment, the ultrasound front end further includes a receiver to receive the electrical signal from the transmit/receive circuit during a receive mode and convert the electrical signal into the digital data.

The wireless handheld ultrasound system may also include a communication interface to wirelessly transmit the image to a backend processor for further processing or an external display unit. The communication interface may be configured to transmit the image to the external display unit via a wired or wireless path.

In one embodiment, the wireless power transducer is coupled to receive acoustic energy from the external source via the ultrasound front end. In other embodiments, the wireless power transducer receives wireless power directly from the external source via induction.

The charging circuit may be configured to continuously charge the battery to a predetermined maximum when the wireless power transducer is receiving wireless power from the external source.

In some embodiments, the charging circuit is configured to communicate with the external power source via a wireless path. The charging circuit may be configured to communicate to the external power source a power level of the battery, an estimated charging time of the battery, a requested wireless power level and/or requested power type. In one embodiment, the charging circuit may be configured to communicate to the external power source a requested wireless power charging schedule.

The handheld ultrasound system may include a locator configured to allow the external power source to track the handheld ultrasound system during wireless power transfer.

BRIEF DESCRIPTION OF THE DRAWINGS

The present disclosure may best be understood by reference to the following description taken in conjunction with the accompanying figures, in which like parts are referred to by like numerals.

DETAILED DESCRIPTION

A number of wireless charging technologies have been proposed for industries outside of medicine with power transfers varying from close range to several meters. Such technologies include tracking RF focused energy, sound waves, inductive coupling, and the like. Each of these technologies tends to work well in close proximity to the transmitter but is less efficient if the device is moved away from the transmitter.

Give the user of a wireless handheld ultrasound system will be moving around a hospital or clinic, the user's proximity to an array of power transmitters will vary considerably over their shift. As such, the average power transfer to the handheld ultrasound unit needs to be very close to equal to the average energy consumption of the unit over the shift as any deficiencies can be made up while the user is not actively on their shift.

The typical power transfer can range from 10s of watts in close proximity to 100s of milliwatts at a distance of several meters. Wireless handheld ultrasound systems are usually stored in the user's coat pocket so the technology used to transfer power to charge the battery should be able to pass through light clothing without too much power loss.

Some of the benefits of being able to reduce the total storage capacity of the battery on these handheld units include smaller size, lighter weight, potential for higher channel count, better performance, lower repetitive stress injuries of the users, and overall improved patient care. A number of physicians have tried to embrace the handheld systems available today but have found it challenging to be able to get the diagnostic level they require to answer their clinical questions, and, as such, they still prefer to use their more traditional and less convenient mobile or cart-based ultrasound platforms.

A typical Lithium-ion battery has around 100-265 Wh/kg. Assuming that the total battery weight budget for a handheld system in around 100 g, the battery capacity would be around 20 Wh. Assuming an 8-hour shift with about a 50% duty cycle, this would provide about 5 W of average power budget for the system.

The typical transmit power budget for a high-performance ultrasound unit is on the order of 2 W and for a 50 mW/channel and 128 channel system, this results in an additional 6.4 W. The basic image formation stage of the system can consume and additional 3 W of if done in a simple manner and the external communication and basic operational hardware might consume and additional 500 mW or a desired power budget of around 12 W to be able to have an adequately performing system.

The ability to keep the battery topped up would reduce the battery size to about 60 gr for a 12 Wh battery, but would require that the wireless charging of the system is able to sustain about 6 W of power transfer on average. This is somewhat of a worst-case scenario and being able to transfer power in a much more limited range of about 1 W would still provide substantial benefits to the users as this should cover all but the most demanding workflows.

Figure 1:
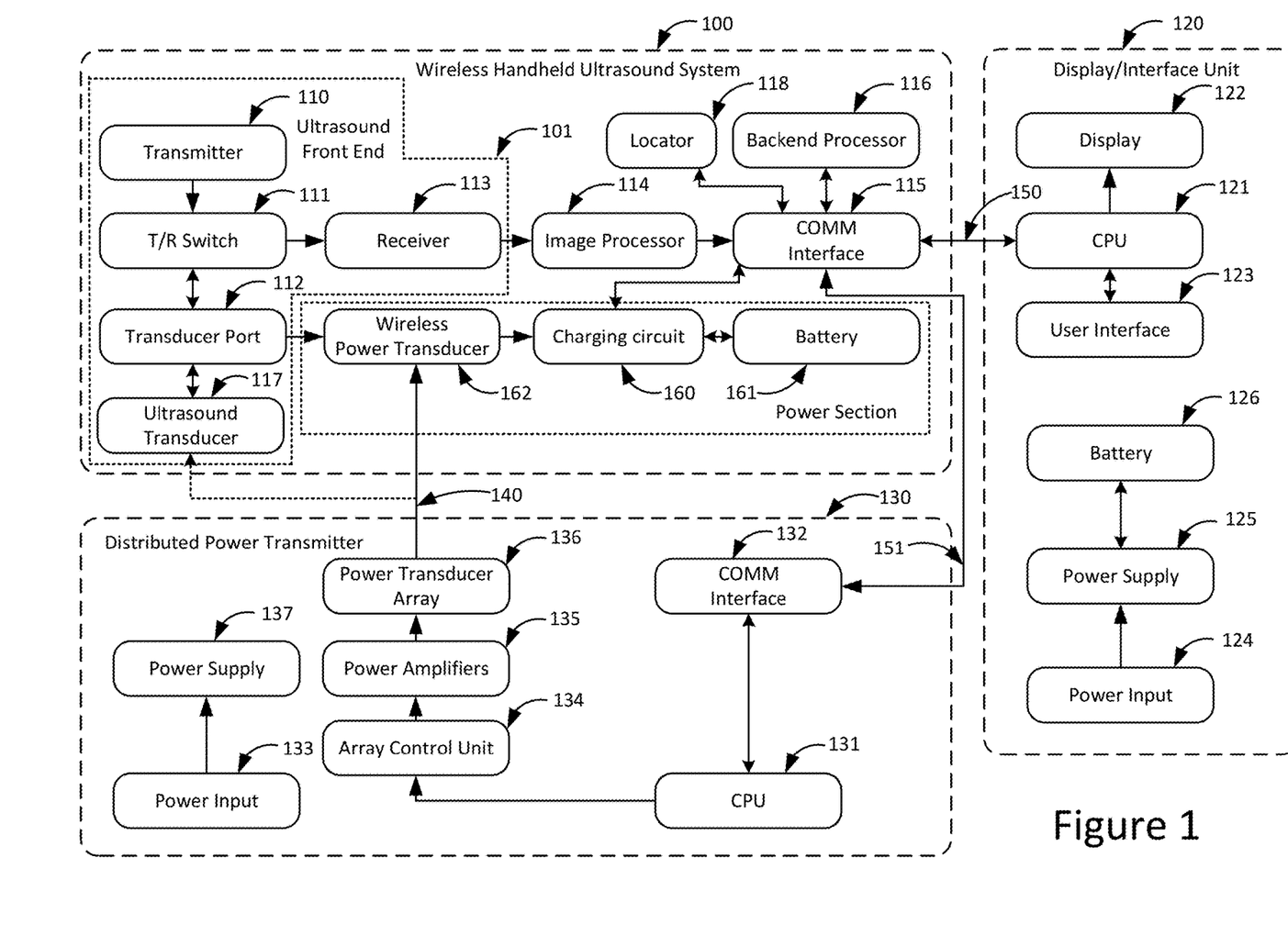
FIG. 1 is a block diagram of a wireless handheld ultrasound system, distributed power transmitter, and display/interface unit.

Referring now to FIG. 1, there is shown a simplified block diagram of a platform for wirelessly transferring power to a wireless handheld ultrasound system 100, which is variously referred to herein a handheld ultrasound system 100 or simply system 100 for purposes of brevity. In one embodiment, the platform includes the handheld ultrasound system 100, a display/interface unit 120, and a distributed power transmitter 130.

Some components of the handheld ultrasound system 100 may be similar to a typical handheld ultrasound imaging system through the step of image formation. For example, a typical ultrasound imaging system is shown in U.S. Pat. No. 8,226,561, titled "Ultrasound Imaging System," issued Jul. 24, 2012, which is incorporated herein by reference. In the depicted embodiment, some image processing is handled by a separate display/interface unit 120 so that the power and size requirements of the handheld ultrasound system 100 can be minimized.

The handheld ultrasound system 100 includes an ultrasound front end 101, which is defined herein broadly as all of the circuitry used to transmit ultrasonic waves into a subject and convert received ultrasonic echoes into digital data. The ultrasound front end 101 may include a transmitter 110 to generate an electrical transmit waveform. The transmitter 110 may be configured to generate the electronical transmit waveform using, for example, such known techniques as programmable transmit voltage, arbitrary firing sequence, programmable apodization, delay control, and/or frequency control.

The electronic transmit waveform is sent through a transmit/receive (T/R) switch 111 during a transmit mode into a subject (e.g., human body) via a transducer port 112. On the transducer port 112, a number of variously configured ultrasound transducers 117 can be attached, such as phased, linear, curved, endo cavity, and the like. These transducers 117 convert electrical energy into acoustic energy.

References to the transducer port 112 and the ultrasound transducer 117 should not be interpreted as a requirement for separate components. In some embodiments, the transducer port 112 may be an input of a non-removal ultrasound transducer 117. Thus, references to the transducer port 112 should do not imply a requirement for the removability of the transducer 117 in every embodiment.

As the acoustic energy passes through the body, reflections are received by the transducer and coupled to the transducer port 112, passing through the T/R switch 111 during a receive mode to the receiver 113. In one embodiment, the receiver 113 performs a variety of basic ultrasound operations known in the art, such as amplification, demodulation, and digitization. The resulting digitized data is passed to the image processor 114. The image processor 114 then processes the digitized data into an image, such as a standard b-mode ultrasound image.

This image is then passed to a COMM (communication) interface 115 where it can either be processed further via a backend processor 116 in the handheld ultrasound system 100 or transferred to the display/interface unit 120 using a wired or wireless communication path 150. The COMM interface 115 may include a bus, a wireless transceiver, and/or other suitable circuitry. The backend processor 116 may perform such standard operations as log compression, downsampling, block hole filtering, and zone blending.

In one embodiment, the display/interface unit 120 receives image data from the handheld ultrasound system 100 via the wired or wireless communication path 150. This link may be bi-directional allowing data from the display/interface unit 120 to be transmitted back to the handheld ultrasound system 100 in response to user commands. Image data is received by the CPU 121 within the display/interface unit 120 and is processed for display on display 122 using techniques such as scan conversion. The display 122 may be an integrated liquid crystal (LCD), light emitting diode (LED), or use other display technology as known in the art.

A user interface 123 also communicates with the CPU 121 to allow the user to enter commands and control various functions of the display/interface 120 system and the handheld ultrasound system 100. The display/interface unit 120 may further include a battery 126, a power supply 125, and a power input 124. The display/interface unit 120 may be embodied as custom device, but could equally be realized with a smart phone, tablet, PDA, laptop computer, or the like.

In one embodiment, the distributed power transmitter system 130 is used to transmit power via a wireless path 140 to the handheld ultrasound system 100. This system communicates with the handheld ultrasound system 100 via a wireless protocol 151, through a COMM interface 132. The COMM interface 132 is controlled by a CPU 131, which uses the information provided by the COMM interface 132 to control an array control unit 134. The array control unit 134 interfaces with the power amplifiers 135 to drive a power transducer array 136.

The power transducer array 136 converts electrical energy into a form of wireless power, e.g., acoustic, electromagnetic, or the like. This wireless power is received by the handheld ultrasound system 100 via a wireless power transducer 162 through the wireless path 140. In the case of wireless power sent by ultrasonic waves, the wireless power transducer 162 may be coupled to the ultrasound transducer 117 via the transducer port 112. The wireless power transducer 162 converts the wireless power into electrical energy and interfaces with a charging circuit 160 of the handheld ultrasound system 100 to charge a battery 161 to a predetermined level.

The distributed power transmitter 130 receives its power via a power input 133 and this power is transferred to the power supply 137 for purposes of powering the components of the distributed power transmitter 130.

In one embodiment, the charging circuit 160 may communicate with the distributed power transmitter 130 via the COMM interface 115 and a wireless communication path 151 to provide information about what is required of the distributed power transmitter system 130 to provide wireless charging to the handheld ultrasound system 100. For example, the charging circuit 160 can communicate information about the level of the battery 161, the estimated charging time to charge the battery, a requested wireless power level, a type of wireless power (e.g., acoustic, inductive) that can be currently received by the wireless power transducer, and/or a wireless power charging schedule.

The requested power level may be based on the distance of handheld ultrasound system 100 from the distributed power transmitter 130, e.g., 5 W when the system is less than 10 cm from the transmitter, 50 mW when the system is a distance of 2 to 3 meters from the transmitter, and 5 mW when the system is a distance of greater than 3 meters from the transmitter. Based on the requested power level, the CPU 131 of the distributed power transmitter 130 may calculate what required level of power is needed to be sent via the power transducer array 136.

The wireless power charging schedule may be used by the CPU of the distributed power transmitter 130 to control the power transducer array 136, and may include times at which wireless charging is requested, requested power levels at those times, and/or types of wireless power requested at those times.

In one embodiment, the handheld ultrasound system 100 includes a locator 118, which may be used by the distributed power transmitter 130 to track the handheld ultrasound system 100 during wireless power transfer, allowing an operator to carry the handheld ultrasound system 100 while it is being charged. The locator 118 may broadcast RF signals at a particular frequency identifiable by the distributed power transmitter 130 or, in some embodiments, broadcast detailed location information derived from GPS and/or spatial location through a wireless network, such as the wireless network of a hospital. In one embodiment, the locator 118 may communicate movement data obtained through a 9-axis accelerometer allowing for the tracking of small movements.

The locator 118 may be coupled to the COMM interface 115, as depicted, or may include its own wireless communication circuitry. The RF signal broadcast by the locator 118 may be usable by the COMM interface 132 in the distributed power transmitter 130 to track the wireless power transducer 162 in the handheld ultrasound system 100 during wireless power transmission and/or calculate a relative distance between the handheld ultrasound system 100 and the distributed power transmitter 130.

Various components and systems for wireless charging of electronic devices using are shown in U.S. Pat. No. 9,362,783, issued Jun. 7, 2016, for "Wireless Power Transmission Apparatus Using Ultrasound," U.S. Pat. No. 7,443,057, issued Oct. 28, 2008, for "Remote Power Charging of Electronic Devices," U.S. Pat. No. 9,941,752, issued Apr. 10, 2018, for "Systems and Methods of Object Detection in Wireless Power Charging Systems," U.S. Pat. No. 9,444,283, issued Sep. 13, 2016, for "Method and Apparatus for Wirelessly Charging Multiple Wireless Power Receivers," U.S. Pat. No. 8,760,113, issued Jun. 24, 2014, for "Wireless Power Charging Timing and Charging Control," U.S. Pat. No. 8,099,140, issued Jan. 17, 2012, for "Wireless Power Supply System and Wireless Power Supply Method," U.S. Pat. No. 8,024,012, issued Sep. 20, 2011, for "Intelligent Wireless Power Charging System," and U.S. Pat. No.

10,128,699, issued Nov. 18, 2018, for "Systems and Methods of Providing Wireless Power Using Receiver Device Sensor Inputs," all of which are incorporated herein by reference. RF-based Wireless Power Systems include, for example, the Powercaster Transmitter and Powerharvester Receiver, available from Powercaster Corp. Acoustic solutions include uBeam, available from uBeam, Inc.

Figure 4:
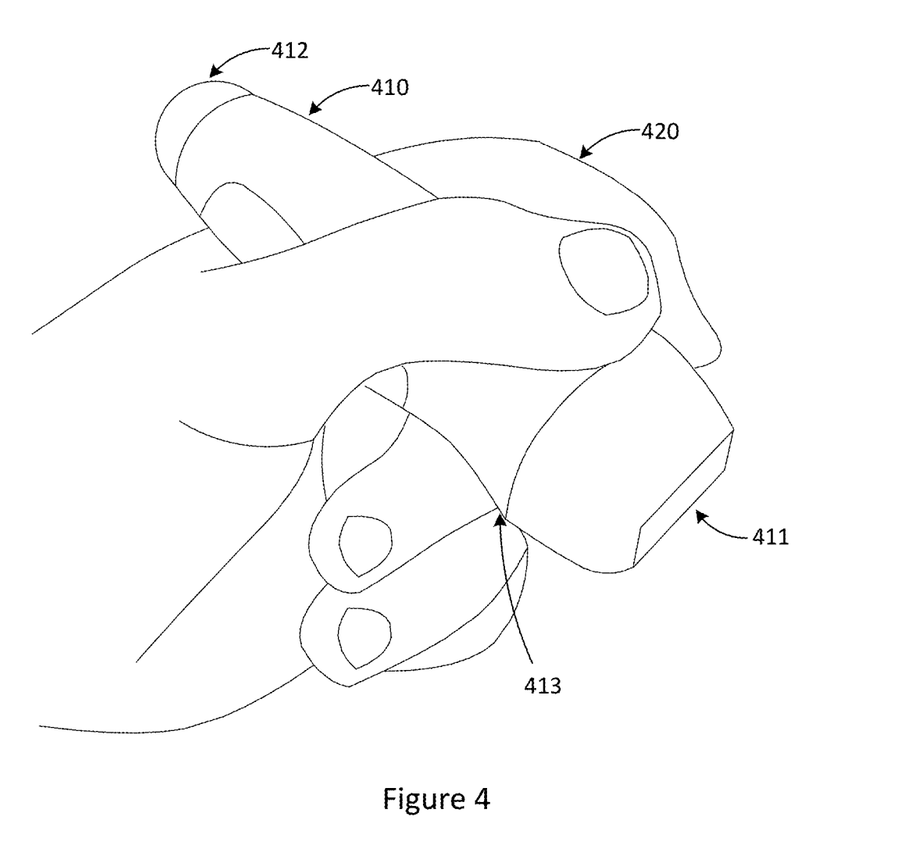
FIG. 4 is an external view of a wireless handheld ultrasound system according to the present disclosure.

FIG. 4 is an external view of a handheld ultrasound system 410 similar to the handheld ultrasound system 100 shown in FIG. 1. This system 410 has many of the size and weight benefits of the traditional ultrasound transducer but also has the benefit of being wireless. For example, a hand 420 comfortably grasps the transducer 410. The electromechanical section (transducer) 411 may also be removable at line 413, so that other transducer geometries can be attached to the transducer body 410, for example, an endo cavity transducer. The transducer body 410 can communicate and receive power via a power transducer 412.

This disclosure has been made with reference to various exemplary embodiments. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element.

As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A wireless handheld ultrasound system for imaging a human body comprising:
    a transducer port;
    a transmitter to generate an electrical transmit waveform;
    a transmit/receive switch to convey the electrical transmit waveform to the transducer port during a transmit mode;
    an ultrasound transducer removably coupled to the transducer port to receive the electrical transmit waveform from the transducer port, generate therefrom ultrasonic waves for transmission into a body of a patient, and convert ultrasonic echoes received from the body of the patient into electrical signals;
    a receiver to receive the electrical signals from the transmit/receive switch during a receive mode and convert the electrical signals into digital data;
    an image processor coupled to the receiver to convert the digital data into an image; and
    a power section coupled to the ultrasound transducer and the image processor, the power section comprising:
        a battery;
        a charging circuit to charge the battery; and
        an ultrasonic wireless power transducer coupled to the charging circuit to convert ultrasonic wireless power received from an external power source into electrical energy for the charging circuit,
        wherein the ultrasound transducer, the image processor, and the power section are contained within a single, portable, handheld unit.

2. The wireless handheld ultrasound system of claim 1, further comprising:
    a communication interface to transmit the image to a backend processor.

3. The wireless handheld ultrasound system of claim 1, further comprising a communication interface configured to transmit the image to an external display unit.

4. The wireless handheld ultrasound system of claim 3, wherein the communication interface is configured to transmit the image to the external display unit via a wireless path.

5. The wireless handheld ultrasound system of claim 3, wherein the communication interface is configured to transmit the image to the external display unit via a wired path.

6. The wireless handheld ultrasound system of claim 1, wherein the charging circuit is configured to communicate to the external power source a requested wireless power charging schedule.

7. The wireless handheld ultrasound system of claim 1, wherein the charging circuit is configured to continuously charge the battery to a predetermined maximum when the ultrasonic wireless power transducer is receiving the ultrasonic wireless power from the external power source.

8. The wireless handheld ultrasound system of claim 1, wherein the charging circuit is configured to communicate with the external power source via a wireless path.

9. The wireless handheld ultrasound system of claim 1, wherein the charging circuit is configured to communicate to the external power source a power level of the battery.

10. The wireless handheld ultrasound system of claim 1, wherein the charging circuit is configured to communicate to the external power source an estimated charging time of the battery.

11. The wireless handheld ultrasound system of claim 1, wherein the charging circuit is configured to communicate to the external power source a requested wireless power level.

12. The wireless handheld ultrasound system of claim 11, wherein the requested power level is 5 W when the wireless handheld ultrasound system is less than 10 cm from the external power source.

13. The wireless handheld ultrasound system of claim 11, wherein the requested power level is 50 mW when the wireless handheld ultrasound system is between 2 and 3 meters from the external power source.

14. The wireless handheld ultrasound system of claim 11, wherein the requested power level is 5 mW when the wireless handheld ultrasound system is greater than three meters from the external power source.

15. The wireless handheld ultrasound system of claim 1, wherein the charging circuit is configured to communicate to the external power source a requested wireless power type.

16. The wireless handheld ultrasound system of claim 1, wherein the wireless handheld ultrasound system includes a locator configured to allow the external power source to track the wireless handheld ultrasound system during wireless power transfer.

* * * * *